United States Patent
Merkens et al.

(10) Patent No.: US 7,578,913 B2
(45) Date of Patent: Aug. 25, 2009

(54) PROBE FOR DETERMINATION OF OXYGEN ACTIVITY IN METAL MELTS AND METHODS FOR ITS PRODUCTION

(75) Inventors: Wilhelm Merkens, Huckelhoven (DE); Norbert Schmitz, Krefeld (DE)

(73) Assignee: Specialty Minerals (Michigan) Inc., Bingham Farms, MI (US)

( * ) Notice: Subject to any disclaimer, the term of this patent is extended or adjusted under 35 U.S.C. 154(b) by 794 days.

(21) Appl. No.: 10/534,070

(22) PCT Filed: Nov. 20, 2003

(86) PCT No.: PCT/EP03/13012

§ 371 (c)(1), (2), (4) Date: May 6, 2005

(87) PCT Pub. No.: WO2004/048961

PCT Pub. Date: Jun. 10, 2004

(65) Prior Publication Data

US 2006/0096861 A1 May 11, 2006

(30) Foreign Application Priority Data

Nov. 26, 2002 (DE) ................... 102 55 282

(51) Int. Cl.
*G01N 27/406* (2006.01)
*G01N 27/417* (2006.01)
(52) U.S. Cl. ............... 204/421; 204/423; 73/19.07
(58) Field of Classification Search ............ 204/422, 204/421; 164/156.1, 450.1; 148/215, 508
See application file for complete search history.

(56) References Cited

U.S. PATENT DOCUMENTS

| 3,578,578 A | 5/1971 | Von Krusenstierna |
| 3,752,753 A | 8/1973 | Fitterer |
| 3,755,126 A * | 8/1973 | Misener et al. ............ 204/423 |
| 3,773,641 A | 11/1973 | Fitterer |
| 4,342,633 A | 8/1982 | Cure |

(Continued)

FOREIGN PATENT DOCUMENTS

CA 1173505 * 8/1984

(Continued)

OTHER PUBLICATIONS

SauerstoffmeBsonde FOX fur Stahlschmelzen. In: Stahl und Eisen 95 (1975) Heft 22 Seite 1084.

*Primary Examiner*—Alex Noguerola
*Assistant Examiner*—J. Christopher Ball
(74) *Attorney, Agent, or Firm*—Derek S. Jessen; Leon Nigohosian, Jr.

(57) ABSTRACT

The invention relates to a probe (100, 200, 300, 400, 500, 600) for the measurement of the oxygen activity of metal melts, in particular steel melts, comprising a reference substance (2) of known oxygen activity in electrically conducting contact (3) with a measuring device; and comprising a solid electrolyte predominantly oxygen ion conducting and negligibly electron conducting at high temperatures and separating the reference substance (2) from the metal melt and having an entry surface (4) for oxygen ions which is in contact with the metal melt, wherein the entry surface (4) of the probe ready for operation is covered by a functional foil arrangement (10,20) in close contact to the entry surface (4).

15 Claims, 2 Drawing Sheets

U.S. PATENT DOCUMENTS

| | | | |
|---|---|---|---|
| 4,657,641 A | 4/1987 | Nakamura et al. | |
| 4,906,349 A | 3/1990 | Beatrice et al. | |
| 4,969,835 A * | 11/1990 | Kobayashi et al. | 439/161 |
| 2002/0100686 A1 * | 8/2002 | Knevels et al. | 204/422 |

FOREIGN PATENT DOCUMENTS

| | | | |
|---|---|---|---|
| DE | 2035882 A1 | | 2/1971 |
| DE | 2833397 A1 | | 2/1980 |
| DE | 3811865 C1 | | 5/1989 |
| EP | 0042086 | | 5/1981 |
| GB | 1594223 | * | 7/1981 |
| JP | 56092450 A | | 7/1981 |
| JP | 56100353 A | | 8/1981 |
| JP | 56100354 A | | 8/1981 |
| JP | 58117449 A | | 7/1983 |
| SU | 441505 A | | 8/1975 |
| SU | 1124219 A | | 11/1984 |

* cited by examiner

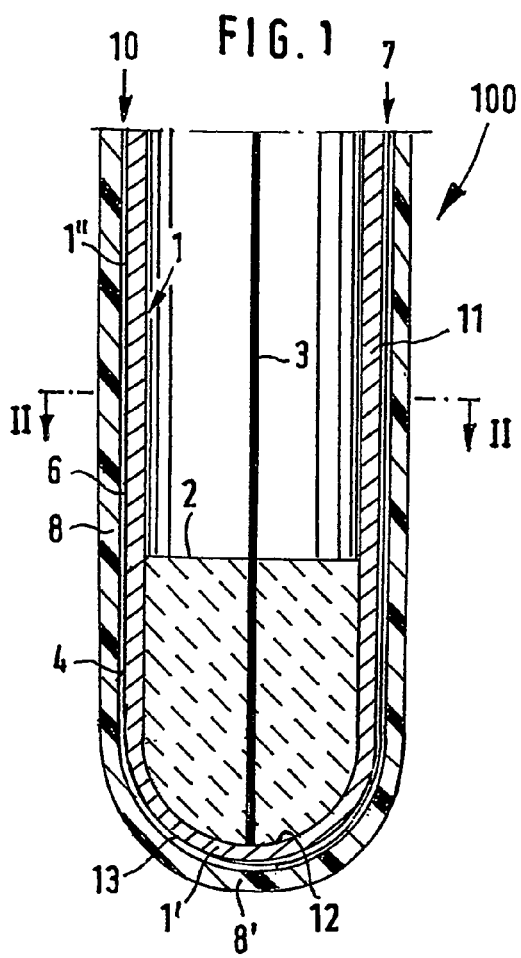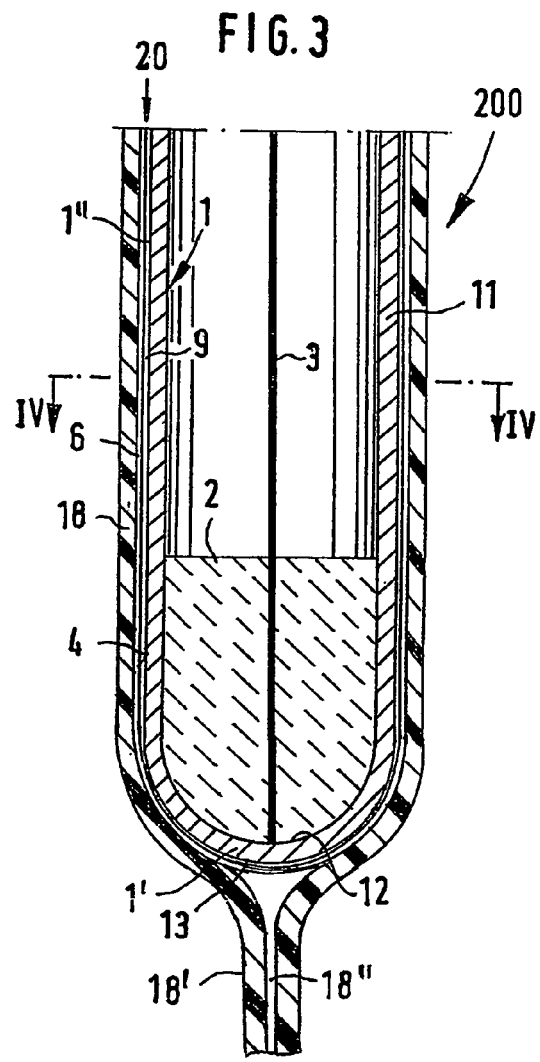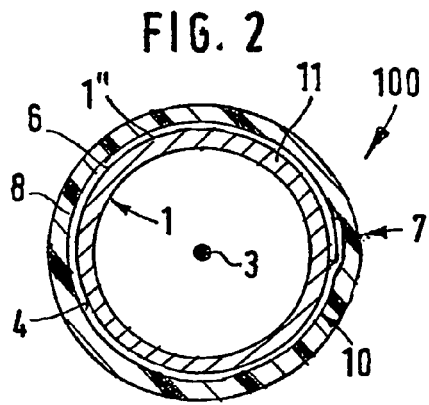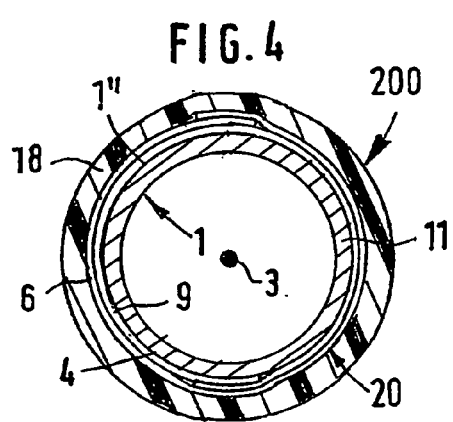

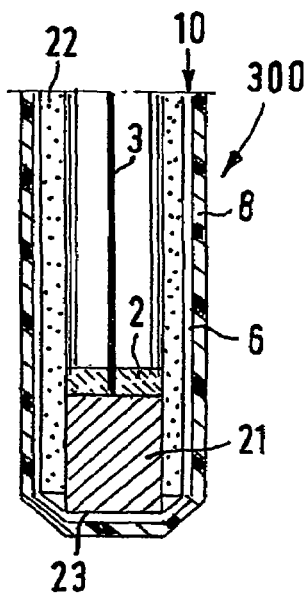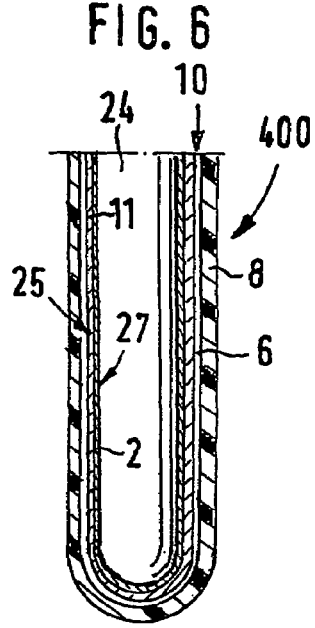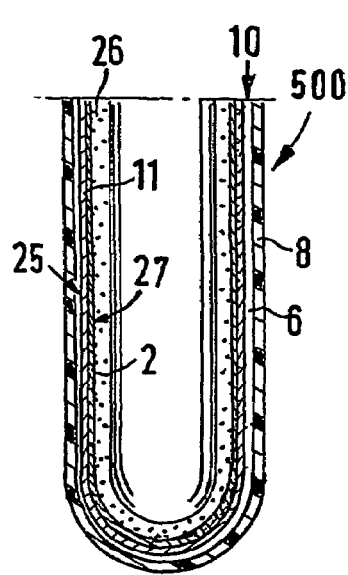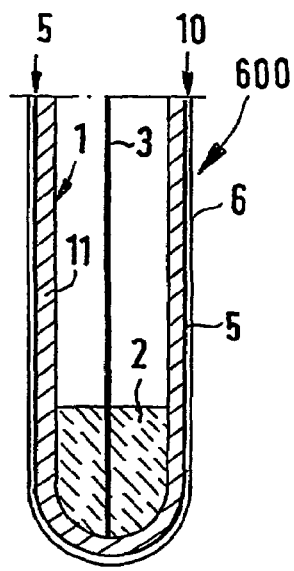

PROBE FOR DETERMINATION OF OXYGEN ACTIVITY IN METAL MELTS AND METHODS FOR ITS PRODUCTION

FIELD OF THE INVENTION

This invention relates to a probe for the measurement of the oxygen activity of metal melts, in particular steel melts and to a method for producing this probe

BACKGROUND OF THE INVENTION

U.S. Pat. No. 4,906,349 discloses a known generic probe. This probe is part of a measuring head that is to be immersed into a metal melt. A small tubelet protruding out of the measuring head is made out of stabilized zirconium oxide which when used at high melt temperatures (about 1500° C. up to 1800° C.) is predominantly oxygen conducting and neglectably electron conducting. The small tubelet is closed at the protruding end and located therein is a reference substance in the form of a powdery mixture of chrome and chrome oxide, which is connected with a measuring instrument by an electric conductor. The measuring instrument is furthermore connected to the outer surface of the tubelet via an electron conducting contact with the metal melt (bath) and further via the metal melt and therefore measures the potential difference between the outer and inner surface of the tubelet, so that, having regard to the temperature, the oxygen activity in the melt can be calculated. The oxygen activity corresponds to the oxygen content dissolved or otherwise present in the respective substance, for example a metal melt, particularly a steel melt.

The principle of the measurement of the oxygen activity with such probes is also disclosed in the article "Sauerstoffmeßsonde FOX für Stahlschmelzen" in the journal "Stahl und Eisen" 95 (1975), No. 22, page 1084.

From U.S. Pat. Nos. 3,752,753 and 3,773,641 it is known that just a plug made from a solid electrolyte may be cemented into the open end of a small refractory tubelet. The plane outer front side of the plug is in contact with the melt during the measurement.

Finally, embodiments are known where a solid electrolyte is in the form of a coating on a carrier pin or on a small carrier tubelet, as can be seen in DE 28 33 397 A1. These probes have a particularly small reaction time, as the thickness of the coating is below 300 μm, and the thermal and electric equilibrium is soon reached.

Probes of the described type have become standard as measuring elements for the oxygen activity especially for monitoring the progress of the deoxidation process with aluminum. Their function is quite satisfactory in the range of higher oxygen levels, that is from 100 ppm to 1000 ppm or more.

However, it was noticed that the reliability, accuracy and especially the reproducibility of the measurement is unsatisfactory in the range of low oxygen levels from 1 ppm to 100 ppm.

The accuracy problem is also dealt with in the already mentioned U.S. Pat. No. 4,906,349. According to this document, the probes to be immersed in the melt are mechanically cleaned on their outer surface by etching or sand blasting in order to allow measuring at oxygen concentration from zero to 20 ppm with a higher precision and with an improved response time.

The mechanical and chemical cleaning of the surface pointing into the melt of a solid electrolyte like zirconium oxide requires an considerable additional expenditure, because it is a very hard and resistant material.

One of the objects of the invention is to improve functionality of the probes at low oxygen concentrations without further expenditure and without risk of unreliable measurements.

SUMMARY OF THE INVENTION

This object is achieved by a further development of the known probe, wherein the entry surface of the solid electrolyte is coated by a functional foil arrangement. A foil arrangement in this sense can be a single foil or [a couple of] several foils located one upon another exerting a particular function when immersed into the melt.

The expression "foil" in the present context is to be taken as the contrast to a coating. A coating is applied to a support and only in this way wins cohesion as a two-dimensional aggregate of material. The foil is a sheet-like, self-supporting two dimensional structure of material, for example a thin-rolled metal, which in contrast to a coating coheres also without a particular support and appears as a flat shaped article of a small thickness which is essentially uniform over the surface.

The foil can have various functions. The problems of the measurement at low oxygen concentrations may partly be explained by the fact that upon immersing of the probe into the melt on the surface of the probe oxygen is drawn in from the neighborhood and is then measured, too. This error is becoming considerable if the oxygen level of the melt is particularly low.

The foil prevents the drawing-in of oxygen for example out of the environmental air on the surface of the probe during its immersion into the melt.

Another function of the foil may be the influence on the wettability of the entry surface by the melt. If the foil is made of such material which does not hinder the migration of the oxygen ions from the melt to the solid electrolyte and at the same time under the influence of the melt during melting has an advantageous effect on the wettability, such errors of the measurement can be reduced.

The foil arrangement as a whole and especially its single foils should be flexible so that they can easily follow the shape of the entry surface of the solid electrolyte and can fit to it in close contact. The foil arrangement correspondingly should possess only a small mechanical rigidity.

It is principally known to provide the entry surface of the solid electrolyte of a probe of the kind discussed with a covering.

In U.S. Pat. No. 4,342,633, for example, a small tubelet of a solid electrolyte is provided with a protective screen of a low carbon steel which is to reduce the temperature shock when immersing of the probe into the metal melt whose protective screen is pushable over the small tubelet. The protective screen surrounds the probe and has itself the shape of a small tubelet being adjusted to the probe and slideable over the probe with a tight fitting. The small tubelet of steel, i.e. the protecting screen, in contrast to a foil, has an inherent stability. This tight fitting is hard to achieve as the small tubcicis of the solid electrolyte are produceable only with some tolerances at the outer periphery. A close contact of the inner periphery of the small tubelet of steel to the outer periphery cannot be obtained. Air and oxygen will always remain in the interstice between the solid electrolyte and the protective screen and affect the measurement at low oxygen levels in the melt. The arrangement given in U.S. Pat. No. 4,342,633 has the purpose of thermal protection and cannot fulfill the purpose of the invention.

Japanese publications JP 56100353 A2 JP 56100354 A2 and JP 56092450 A2 disclose coatings of the solid electrolyte probe improving the measurement behavior of the probe in molten steel. In JP 56100353 A2 a coating is presented with a metal like Fe, Cu, Ni, Mg, Al or a metal oxide like MgO, $Al_2O_3$ or similiar made by vaporizing sputtering ion plating or another method. From JP 56100354 A2 the covering of the solid electrolyte with a metal oxide powder like MgO, $Al_2O_3$ or similiar in an organic binder is known that results into an accelerated heat transfer and an improved process reaction rate. JP 56092450 A2 teaches an oxygen activity of about 35 ppm, thus a low level range, is mentioned. In JP 56092450 A2 a coating of a mixture of a metal powder and an organic binder to improve the wettability of the solid electrolyte probe through the molten steel is described. Between the probe and the steel no thermal isolating layer is to be established. This will reduce the reaction time of the device.

The coverings in the form of coatings need an additional costly apparatus and bear the risk or exfoliating off from the surface of the solid electrolyte upon its immersion into the melt. On the other hand, the covering of the entry surface with a foil arrangement according to the invention has the advantage of greater simplicity, and exfoliating like in a coating will not take place.

In GB patent 1 594 223 there is disclosed a method and an apparatus for the determination of the hydrogen concentration present in a substance comprising monitoring the e.m.f. generated between the substance a reference material which are separated from each other by s solid electrolyte comprising a metal hydride, in which the electrolyte is sealed from the atmosphere prior to use, and the seals removed on introduction of the electrolyte to the substance. The seal can be constituted by a metal foil held in place by an adhesive. The purpose of the foil is to protect the metal hydride of the reference material from the atmosphere.

The foil arrangement can have at least one foil oxidizable by oxygen in the metal melt and can for example consist of an aluminum material. Other materials which may be used as the oxidizable foil are amongst others titanium, tin, magnesium for example, because they are easily oxidizable.

Such a foil melts instantly upon contact with the hot melt and reacts with the oxygen that may have been drawn in at the surface of the probe during immersion into the melt. This oxygen therefore cannot falsify the measurement any longer.

The foil arrangement can have at least one second functional foil at least partly covering or overlapping the first foil on its outer or inner side.

It may be advantageous that the material of the second foil when melting enhances the wettability of the entry surface of the solid electrolyte in contact with the melt so that the solid electrolyte will have uniform contact with the melt.

A foil with such a function can be made of a copper material. Further examples for the material of the second foil are Pb, Ag, Zn, Sn, Au, Pt, Bi, Mg.

In case the solid electrolyte is provided in the form of a plug-like piece of material tightly fixed in the open end of a refractory small tubelet and having a substantially flat front wall directed to the melt when immersed, the foil arrangement can extend in front of this front wall, covering it from the melt in the first moments of immersion.

In cases where the solid electrolyte is a coating on a carrier-pin or a small carrier tubelet, the first arrangement covers all the parts of the solid electrolyte that otherwise would be in direct contact with the molten metal during the time of immersion.

If the solid electrolyte, as it is preferred, is provided in the form of a small tubelet to be immersed into the melt and closed at the end to be immersed, the foil arrangement on the immersing part of the small tubelet surrounds its outer periphery tightly, which means the cylindrical part of the outer periphery and the hemispherical part closing the tubelet as well.

An important further development of the invention involves means for keeping the foil arrangement in close contact to the entry surface of the solid electrolyte.

Such means can be a chemical binder located between the entry surface and the foil arrangement and disintegrating when in contact with the melt. Such a binder is to disappear by burning, vaporizing or dissolving in the melt after it provided the close contact to the entry surface until immersion. Examples are organic adhesives like acrylic resins.

Alternatively and preferably the means can be mechanical means which press the foil arrangement from outside into close contact with the entry surface of the solid electrolyte.

The pressing can take place essentially uniformly over the surface, particularly by elastic means. A simple embodiment of this kind which has already proven itself in practice is an elastomeric hose tightly surrounding the foil arrangement on the outer surface of the small tubelet.

This hose may have at first a greater diameter than the foil arrangement put around the small tubelet and may be shrinkable in its radial diameter onto the foil arrangement after being slid over it longitudinally.

This can be practically effected in that the hose is made of a material with a thermoactive shape memory, i.e. a material, which can be deformed permanently and which under the effect of heat returns to its original shape and dimensions.

The invention also has a process aspect according to which the small tubelet is surrounded tightly by a functional foil arrangement at its peripheral surface, where over the foil arrangement located on the small tubelet an elastomeric hose is slid longitudinally whereafter the hose is shrunk onto the foil arrangement causing a radial pressure and a close contact between the foil arrangement and the entry surface of the solid electrolyte.

A hose made of a shape-memory material can be used and the hose is then heated for shrinking when in the slid-over position.

The following non-limiting description along with accompanying figures is provided to more specifically teach and set forth particular embodiments of the present invention as envisioned here. They are for illustrative purposes only, however, and those skilled in the art should understand that they can make various changes, substitutions and alterations herein without departing from the spirit and scope of the invention in its broadest form.

DETAILED DESCRIPTION OF THE INVENTION

Preferred Embodiments of the invention are illustrated in the accompanying figures.

FIG. 1 shows a longitudinal section of the lower part of a probe;

FIG. 2 shows a cross section along Line II-II in FIG. 1;

FIG. 3 shows an analogue longitudinal section of a second embodiment;

FIG. 4 shows a cross section along Line IV-IV in FIG. 3.

FIG. 5 to 8 show longitudinal sections analogue to FIG. 1 in a reduced scale.

The probe which is referred to as a whole by numeral 100 in FIG. 1 has a small tubelet 1 having a cylindrical outer surface 1" which is approximately hemispherically closed at the lower end. It is made of a solid electrolyte 11 which at high temperatures is predominantly oxygen ion conducting and negligibly electron conducting and which in this embodiment is made out of $ZrO_2$ stabilized with MgO. The reference substance 2 is a powdery mixture of chrome and chrome oxides and is located in the lower part of the small tubelet 1. The inner surface 12 of the solid electrolyte 11 is at the apex part of the lower end 1' in electrically conducting contact with a contact wire 3 leading to a measuring instrument such as a Voltmeter. The outer surface of the lower end 1' is referred to as numeral 13. In practice, the small tubelet 1 has an outer diameter of about 5 mm and a total length of about 30 mm. Only the lower part is shown in FIG. 1. The small tubelet 1 together with a thermocouple for measuring the temperature of the metal melt in the immediate vicinity of the probe (like within a range of 1 to 10 mm) and a bath contact, preferably made from a high-melting metal, is fixed in a probe head (not shown in the figures) which is immersed into the metal melt at the end of a lance. The bath contact is coupled to the measuring instrument as well. The reference substance 2 has a known oxygen activity. The oxygen activity of the melt depends on its oxygen content. This results in a potential difference between the outer and inner surface of the small tubelet which is measured via the measuring instruments and calculates the oxygen activity of the metal melt.

The small tubelet 1 at its outer peripheral surface area constitutes an entry surface 4 for the oxygen ions of the melt.

The entry surface 4 is wrapped tightly by a foil arrangement 10, which is in the embodiment of FIG. 1 by a single foil 6 out of a aluminum material. In this embodiment the single foil 6 is wrapped once around the small tubelet 1. The edges slightly overlap at position 7 in FIG. 2, so that the whole surface of the small tubelet 1 is covered. At the lower end the foil 6 is folded around the surface 13 so that the complete outer surface of the small tubelet 1 is concealed.

The foil 6 is itself surrounded by a hose 8 being made out of a elastomeric material, which in the embodiment of FIG. 1 is closed at its lower end 8' similarly to the small tubelet 1. The hose 8 has at first a cylindrical inner diameter slightly greater than the outer diameter of the foil 6 wrapped around the small tubelet 1. In this state, the hose 8 can be pulled or slid over the foil 6 over its whole length and is then covering the foil 6 and the small tubelet 1 to their total extent including the lower end 1'. The hose 8 consists out of a shape-memory material. It has undergone a pretreatment in the form of a radial dilation, which has led to a permanent expansion. If heated, it tends to return to its original diameter. Therefore, the hose 8 can be shrunk by heating so that a circumferential tension in the hose 8 is build up leading to a radial pressure on the foil 6, which brings the foil 6 into close contact to the entry surface 4, i.e. the outer surface of the small tubelet 1. In FIGS. 1 and 2, the probe 100 is shown in its state ready for operation after the shrinking of the hose 8.

The presence of the foil 6 in close contact to the entry surface 4 of the small tubelet 1 has the consequence that upon immersion of the probe 100 into the metal melt no oxygen from the ambient air can stick to the entry surface 4 build up by the outer surfaces 1'', 13 and thereby be drawn into the melt and affect the oxygen activity measurement. This would be so-called unwanted oxygen. The intention is, however, to measure only the oxygen in the melt. Immediately after the probe 100 is immersed into the melt, the hose 8 burns up. The resulting amount of carbon and of oxygen consumed by the respective carbon-oxygen reaction is so low that the oxygen measurement, even if it is for oxygen concentration below 100 ppm, nevertheless is affected in a negligible way. Additionally carbon monoxide and/or carbon dioxide does not stick to the tubelet 1 as this is prevented by the foil 6. After the disappearance of the hose 8, the foil 6 is oxidized by any unwanted oxygen in the proximity of the entry surface 4. Therefore the foil 6 is in a sense catching away unwanted introduced oxygen by using it up when it is oxidized. As a result, the measurement of the oxygen activity of the melt is not influenced by external effects. Due to the very low mass of the foil 6, the foil that is not oxidized is immediately dissolved in the melt and thus the measurement to follow is unaffected.

As far as in the further probes functional equivalent parts are present, these are referred to by the same numerals as in the probe 100 of FIGS. 1 and 2.

The probe 200 differs from the probe 100 in that the foil arrangement 20 in this case is two-layered. There is a radial outer foil 6 made out of an aluminum material and a radial inner foil 9 made out of a copper material. When the radial inner foil 9 comes in contact with the metal melt after the disappearance of the hose 18 and the foil 6 the wettability of the entry surface 4 is improved. The foils 6 and 9 are layered over each other on the whole surface. They may be laminated or loosely positioned over each other. The foil arrangement 20 covers the cylindrical part 1'' as well as the area 13 located at the lower end 1' of the small tubelet 1

In contrast to the hose 8, in FIG. 3 the hose 18 is not closed at the lower end, but simply consists of a cut off length of hose, which slightly extends over the lower part 1' of the small tubelet 1. The hose 18 is shrank after sliding it over the small tubelet 1 and foil arrangement 20. The configuration as shown in FIG. 3 is reached, in which the protuding part 18', which can shrink freely, has shrunk to a significantly smaller diameter, merely leaving a small inner channel 18'' which is outwardly open. In the upper part of FIG. 3, however, the hose 18 cannot shrink freely, but builds up a circumferential tension radially pressing the foil arrangement 20 to the outer surface of the small tubelet 1. This embodiment also fulfills the function of close contact of the foil arrangement 20 to the outer surface 1'',13 of the small tubelet of the solid electrolyte and is more economical than a closed hose 8.

It is clear that the foil arrangements 10, 20 may be wrapped around the small tubelet 1 several times.

For better visibility, the thickness of the foils 6, 9 and the hoses 8,18 has been shown exaggerated. In practice, the foils have a thickness of about 0.001 to 0.05 mm. The shrinkable hose 8, 18 can have a wall thickness of about 0.2 to 0.5 mm.

The above explanations are also valid for the further embodiments of the invention according to FIG. 5 to 8.

The probe 300 of FIG. 5 has no solid electrolyte 11 as in FIG. 1 though FIG. 3 in the form of a small tubelet closed at one end, but has a plug 21, which is tightly mounted into the open end of a refractory tubelet 22. The plug 21 has an essentially plane formed front side 23 that forms a perpendicular plane to the axis of the tubelet 22. A foil arrangement 10 made from a single foil as in the embodiment according to FIG. 1 extends in front of the front side. The overlapping of the longitudinal edges of the foil is not illustrated. Of the backside of plug 21 opposite to the front side 23, the reference substance 2 is provided in the form of a disk. The foil 6 covers the front side 23 and also a part of the cylindrical periphery of tubelet 22 so that the part of probe 300 that is immersed in the metal melt is completely covered by foil 6.

Hose 8 closed at its lower end in FIG. 5 has been shrunk on the outer periphery of foil 6 in the cylindrical part as well as in the lower part in front of the front side 23. The hose has the same features and functions as the hose 8 in FIGS. 1 and 2.

Probe 400 of FIG. 6 has a support in the form of a pin 24 made from refractory material. A coating 27 of a reference substance 2 is provided on the outer circumference of the emerging end of pin 24. The coating 27 is itself covered by a coating 25 of a solid electrolyte. The contact of the reference substance 2 and the solid electrolyte 11 to the measuring device is not illustrated. The coatings 25 and 27 cover the said end of pin 24 completely and tightly. The coatings are completely covered by a foil arrangement 10 which again has only one foil 6. A hose has been shrunk on the complete outer circumference of the foil arrangement. The hose 8 is closed at its lower end and has the same features as hose 8 of FIGS. 1 and 2.

The probe 500 of FIG. 7 has a reference substance 2 and a solid electrolyte 11 as coatings 27 and 25, respectively, however, on the outer circumference of a refractory tubelet 26, which is closed on one end and is used here in place of the refractory pin 24 of FIG. 6. The coatings 27 and 25 are covered by a foil arrangement 10 with only one foil 6 where the coatings will be in contact with the metal melt. The whole outer circumference of which is again covered and held together by a hose 8 shrunk to it.

In principal, the shrinking hose 8, 18 can also be omitted if the foil arrangement 10, 20 is provided with a binder over its surface and is glued around the small tubelet 1, as it is illustrated at the probe 600 in FIG. 8. Probe 600 has a small tubelet 1 made from a solid electrolyte 11, like probe 100. In the tubelet 1, the reference substance 2 is placed. A foil 6 is glued around the whole exterior surface of the tubelet 1 by means of an acrylic resin adhesive 5 illustrated only by a thicker line. The acrylic resin adhesive 5 exerts the function of hoses 8, 18 in the other embodiments, i.e. to maintain foil 6 in tight contact at the entry surface.

The embodiments with a hose, however, are preferred due to their better protection of the entry surface for against oxygen drawn in during immersion into the melt.

What is claimed:

1. A probe for the measurement of the oxygen activity of metal melts, in particular steel melts,
    comprising a reference substance in electrically conducting contact with a measuring device;
    and comprising a solid electrolyte predominantly oxygen ion conducting at high temperatures and negligibly electron conducting and separating the reference substance from the melt and having an entry surface for oxygen ions in contact with the melt, and comprising a cover for the entry surface of the probe ready for operation wherein the cover is in the form of a foil arrangement and that the probe comprises mechanical means for pressing the foil arrangement from outside into close contact with the entry surface.

2. The probe according to claim 1, wherein the foil arrangement comprises at least one foil oxidizable by the oxygen contained in the melt.

3. The probe according to claim 2, wherein the foil consists of an aluminum material.

4. The probe according to claim 2, wherein the foil arrangement comprises at least a further foil at least partly covering the first foil.

5. The probe according to claim 4, wherein the material of the further foil when melting due to the contact with the melt enhances the wettability of the entry surface of the solid electrolyte.

6. The probe according to claim 5, wherein the further foil consists of a copper material.

7. The probe according to claim 1, wherein the solid electrolyte is provided in form of a material having a substantially flat end wall at the end of a refractory small tubelet and the foil arrangement extends in front of said end wall.

8. The probe according to claim 1, wherein the solid electrolyte is provided in form of a small tubelet to be immersed into the melt and closed at the end to be immersed with the reference substance being located in the interior of the small tubelet and that the foil arrangement totally and tightly surrounds the outer periphery of the small tubelet.

9. The probe according to claim 1, wherein said means comprise a binder located between the entry surface and the foil arrangement and disintegrating when in contact with the melt.

10. The probe according to claim 1, wherein said means press the foil arrangement against the entry surface over its extension.

11. The probe according to claim 10, wherein said means press the foil arrangement against the entry surface in an elastic way.

12. The probe according to claim 11, wherein said mechanical means tightly surrounds the foil arrangement on the outer periphery of the small tubelet constituting the solid electrolyte.

13. The probe according to claim 12, characterized in that said mechanical means first has a greater diameter than the foil arrangement surrounding the small tubelet and that said mechanical means is shrinkable in its radial diameter after being positioned longitudinally over the foil arrangement.

14. A method of producing a probe for the measurement of oxygen activity of metal melts, in particular steel melts, with the probe comprising a solid electrolyte predominantly oxygen conducting at high temperatures and negligibly electron conducting and intended to be immersed into the metal melt and having an entry surface for oxygen ions, characterized in that the entry surface is tightly covered by a functional foil arrangement; that over the foil arrangement on the entry surface an elastomeric hose is positioned longitudinally and that then the hose is shrunk onto the foil arrangement causing a radial tension leading to a close contact between the foil arrangement and the entry surface.

15. The method according to claim 14, wherein the hose is a thermoactive shape memory material and the hose is heated when in position.

* * * * *